US009610302B2

(12) United States Patent
Bartel et al.

(10) Patent No.: US 9,610,302 B2
(45) Date of Patent: *Apr. 4, 2017

(54) COMPOSITION CONTAINING PHOSPHOLIPID-DHA AND B VITAMINS

(71) Applicant: Buriva, LLC, Atlanta, GA (US)

(72) Inventors: Brett B. Bartel, Marietta, GA (US); Rhett Sean Daniels, Fort Myers, FL (US)

(73) Assignee: Buriva, LLC., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/721,156

(22) Filed: May 26, 2015

(65) Prior Publication Data

US 2015/0250812 A1 Sep. 10, 2015

Related U.S. Application Data

(63) Continuation-in-part of application No. 14/688,193, filed on Apr. 16, 2015, now Pat. No. 9,233,114, which is a continuation-in-part of application No. 14/562,650, filed on Dec. 5, 2014, now Pat. No. 9,216,199.

(60) Provisional application No. 61/912,205, filed on Dec. 5, 2013, provisional application No. 62/088,528, filed on Dec. 5, 2014.

(51) Int. Cl.

| | |
|---|---|
| *A61K 31/714* | (2006.01) |
| *A61K 31/519* | (2006.01) |
| *A61K 31/661* | (2006.01) |
| *A61K 31/675* | (2006.01) |
| *A61K 31/198* | (2006.01) |
| *A61K 31/341* | (2006.01) |
| *A61K 31/4415* | (2006.01) |
| *A61K 31/592* | (2006.01) |
| *A61K 31/593* | (2006.01) |
| *A61K 31/685* | (2006.01) |
| *A61K 45/06* | (2006.01) |
| *A23P 20/10* | (2016.01) |
| *A23L 33/115* | (2016.01) |
| *A23L 33/12* | (2016.01) |
| *A23L 33/15* | (2016.01) |
| *A23L 33/16* | (2016.01) |

(52) U.S. Cl.
CPC .......... *A61K 31/714* (2013.01); *A23L 33/115* (2016.08); *A23L 33/12* (2016.08); *A23L 33/15* (2016.08); *A23L 33/16* (2016.08); *A23P 20/10* (2016.08); *A61K 31/198* (2013.01); *A61K 31/341* (2013.01); *A61K 31/4415* (2013.01); *A61K 31/519* (2013.01); *A61K 31/592* (2013.01); *A61K 31/593* (2013.01); *A61K 31/661* (2013.01); *A61K 31/675* (2013.01); *A61K 31/685* (2013.01); *A61K 45/06* (2013.01); *A23V 2200/322* (2013.01); *A23V 2250/7052* (2013.01)

(58) Field of Classification Search
None
See application file for complete search history.

(56) References Cited

U.S. PATENT DOCUMENTS

| | | | |
|---|---|---|---|
| 5,434,183 A | 7/1995 | Larsson-Backstrom | |
| 5,436,269 A | 7/1995 | Yazawa et al. | |
| 5,466,841 A | 11/1995 | Horrobin et al. | |
| 5,484,611 A | 1/1996 | Noble et al. | |
| 5,567,730 A | 10/1996 | Miyashita et al. | |
| 5,654,290 A | 8/1997 | Bayon et al. | |
| 5,731,346 A | 3/1998 | Egberg et al. | |
| 5,747,533 A | 5/1998 | Egberg et al. | |
| 5,853,747 A | 12/1998 | Ponroy | |
| 5,869,530 A * | 2/1999 | Ponroy ................. | A23L 1/3008 514/549 |
| 5,869,714 A | 2/1999 | Bruzzese | |
| 6,036,992 A | 3/2000 | Borror et al. | |
| 6,150,411 A | 11/2000 | Stordy | |
| 6,153,653 A | 11/2000 | Shashoua | |
| 6,200,624 B1 | 3/2001 | Mazar et al. | |
| 6,306,907 B1 | 10/2001 | Nishikawa et al. | |
| 7,799,365 B2 | 9/2010 | Hudson et al. | |
| 7,824,727 B2 | 11/2010 | Hudson et al. | |
| 7,842,679 B2 | 11/2010 | Pieroni et al. | |
| 7,968,737 B2 | 6/2011 | Kawashima et al. | |
| 8,030,348 B2 | 10/2011 | Sampalis | |
| 8,202,907 B2 | 6/2012 | Sakakibara et al. | |
| 8,241,672 B2 | 8/2012 | Driscoll | |

(Continued)

FOREIGN PATENT DOCUMENTS

WO 2014165008 10/2014

OTHER PUBLICATIONS

Nutrient content one large Egg, 2012.*
Lichtenberger, et al.; "Phosphatidylcholine Association Increases the Anti- Inflammatory and Analgesic Activity of Ibuprofen in Acute and Chronic Rodent Models of Joint Inflammation: Relationship to Alterations in Bioavailability and Cyclooxygenase-Inhibitory Potency", The Journal of Pharmacology and Experimental Therapeutics, 2001, vol. 298, No. 1, 9 pgs.
Carnielli, et al.; "Intestinal absorption of long-chaing polyunsaturated fatty acids in preterm infants fed breast milk or formula", The American Journal of Clinical Nutrition, 1998, 67:97-103, 7 pgs.

(Continued)

*Primary Examiner* — Robert A Wax
*Assistant Examiner* — William Craigo
(74) *Attorney, Agent, or Firm* — Brett B. Bartel

(57) ABSTRACT

Described herein are manufactured dietary supplements that contain a phospholipid extract and the extract contains two forms of phospholipid-docosahexanoic acid. One form of phospholipid-docosahexanoic acid is phosphatidylcholine-docosahexanoic acid, and another form of phospholipid-docosahexanoic acid is phosphatidylethanolamine-docosahexanoic acid. The manufactured dietary supplement also contains L-methylfolate, vitamin $B_6$, and vitamin $B_{12}$.

19 Claims, 3 Drawing Sheets

(56) References Cited

U.S. PATENT DOCUMENTS

| | | | |
|---|---|---|---|
| 8,278,351 B2 | 10/2012 | Sampalis | |
| 8,283,335 B2 | 10/2012 | Hageman et al. | |
| 8,324,276 B2 | 12/2012 | Bryhn | |
| 8,349,895 B2 | 1/2013 | Van Elswyk | |
| 8,367,729 B2 | 2/2013 | Sakakibara et al. | |
| 8,383,675 B2 | 2/2013 | Sampalis | |
| 8,586,567 B2 | 11/2013 | Sampalis et al. | |
| 8,609,726 B2 | 12/2013 | Bryhn | |
| 8,680,080 B2 | 3/2014 | Sampalis | |
| 8,697,676 B2 | 4/2014 | Rosedale | |
| 8,703,744 B2 | 4/2014 | Pollock et al. | |
| 8,759,319 B2 | 6/2014 | Hageman et al. | |
| 8,846,604 B2 | 9/2014 | Hallaraker et al. | |
| 2004/0266874 A1 | 12/2004 | Akimoto et al. | |
| 2005/0130937 A1 | 6/2005 | Ben Dror et al. | |
| 2006/0057185 A1 | 3/2006 | Akimoto et al. | |
| 2009/0048215 A1 | 2/2009 | Ishikura et al. | |
| 2009/0226481 A1 | 9/2009 | Ishikura et al. | |
| 2010/0298273 A1 | 11/2010 | Bar Yosef | |
| 2010/0316680 A1 | 12/2010 | Bruheim et al. | |
| 2012/0329749 A1* | 12/2012 | Smith | A61K 31/519 514/52 |
| 2013/0059768 A1 | 3/2013 | Hallaraker et al. | |
| 2013/0172361 A1* | 7/2013 | Fava | C12Q 1/6883 514/250 |
| 2013/0245119 A1 | 9/2013 | Harauma et al. | |
| 2013/0303795 A1 | 11/2013 | Wang et al. | |
| 2014/0065231 A1* | 3/2014 | Schultz | A61K 31/198 424/490 |
| 2014/0080791 A1 | 3/2014 | Berge et al. | |
| 2014/0088043 A1 | 3/2014 | Hoem et al. | |
| 2014/0088047 A1 | 3/2014 | Hoem et al. | |
| 2014/0135289 A1 | 5/2014 | Han et al. | |
| 2014/0141074 A1 | 5/2014 | Sampalis et al. | |
| 2014/0274968 A1 | 9/2014 | Berge et al. | |
| 2014/0370130 A1 | 12/2014 | Van Elswyk | |
| 2015/0038469 A1 | 2/2015 | Sampalis | |
| 2015/0050261 A1 | 2/2015 | Evenstad et al. | |

OTHER PUBLICATIONS

Department of Health & Human Services; "Memorandum: 75-Day Premarket Notification of New Dietary Ingredients", Public Health Service, Food and Drug Administration; Jan. 23, 2003, 11 pgs.

Chen, et al.; "Docosahexaenoic Acid-Containing Phospholipids and Triglycerides Based Nutritional Supplements", Recent Patents on Food, Nutrition & Agriculture, 2010, 2, 213-220, 8 pgs.

Valenzuela, et al.; "Supplementing female rats with DHA-lysophosphatidylcholine increases docosahexaeonic acid and acetylcholine contents in the brain and improves the memory and learning capabilities of the pups", Grasas Y Aceites, 61 (1), Enero-Marzo, 16-23, 2010; ISSN: 0017-3495, DOI: 10.3989/gya.053709, 8 pgs.

European Food Safety Authority; "Scientific Opinion on the Tolerable Upper Intake Level of eicosapentaenoic acid (EPA), docosahexaenoic acid (DHA) and docosapentaenoic acid (DPA)", EPSA Panel on Dietic Products, Nutrition and Allergies (NDA), EFSA Journal 2012; 10(7):2815, 48 pps.

Hoffman, et al.; "Maturation of Visual Activity Is Accelerated in Breast-Fed Term Infants Fed Baby Food Containing DHA-Enriched Egg Yolk", JN The Journal of Nutrition, 2004 American Society for Nutritional Sciences, 7 pgs.

Chen, Su; "Lipids Based Docosahexaenoic Acid (DHA) Carriers and their Ability to Deliver DHA to the Brain: A Prospective Outline", Bioequivalence and Bioavailability 2013; 5:2, 2 pgs.

Lemaitre-Delaunay, et al.; "Blood compartmental metabolism of docosahexaenoic acid (DHA) in humans after ingestion of a single dose of [13C]DHA in phosphatidylcholine", Journal of Lipid Research, vol. 40, 1999, 8 pgs.

Bazinet, et al.; "Polyunsaturated fatty acids and their metabolites in brain function and disease", Nature Reviews Neuroscience, AOP, published online Nov. 12, 2014, 15 pgs.

Payet, et al; "Docosahexaenoic acid-enriched egg consumption induces accretion of arachidonic acid in erythrocytes of elderly patients", British Journal of Nutrition (2004), 91, 789-796, 8 pgs.

Valenzuela, et al.; "Docosahexaenoic acid (DHA), essentially and requirements: why and how to provide supplementation", Grasas Y Aceites, 57 (2) Abril-Junio, 229-237, 2006, 9 pgs.

Daniels, Rhett Sean; Non-Final Office Action for U.S. Appl. No. 14/562,650, filed Dec. 5, 2014, mailed Apr. 21, 2015, 19 pgs.

Graf, et al; Age dependent incorporationof 14C-DHA into rat brain and body tissues after dosing various14C-DHA-esters, Prostaglandins,Leukotrienes and Essential Fatty Acids 83 (2010) 89-96, 8 pgs.

De Groot, et al.; Effect of a-linolenic acid supplementation during pregnancy on maternal and neonatal polyunsaturated fatty acid status and pregnancy outcome1-3, The American Journal of Clinical Nutrition 2004; 79:251-60; 10 pgs.

Lagarde, et al.; "Lysophosphatidylcholine as a Preferred Carrier Form of Docosahexaenoic Acid to the Brain", Journal of Molecular Neuroscience, Copyright 2001 Human Press Inc., 4 pgs.

Valenzuela, et al.; "Tissue Accretion and Milk Content of Docosahexaenoic Acid in female rats after Supplementation with Different Docosahexaenoic Acid Sources", Annals of Nutrition & Metabolism, Published online Aug. 4, 2005, 8 pgs.

Brossard, et al.; "Human plasma albumin transports [3C]Docosahexaenoic acid in two lipid forms to blood cells", Journal of Lipid Research, vol. 38, 1997, 12 pgs.

Liu, et al.; "Higher efficacy of dietary DHA provided as a phospholipid than as a triglyceride for brain DHA accretion in neonatal piglets", Journal of Lipid Research, Jan. 2013, 40 pgs.

Thies, et al.; "Preferential incorporation of sn-2 lysoPC DHA over unesterified DHA in the young rat brain", The American Physiological Society, 1994, 7 pgs.

* cited by examiner

COMPOSITION CONTAINING PHOSPHOLIPID-DHA AND B VITAMINS

CROSS-REFERENCE TO RELATED APPLICATION

This application is a continuation-in-part of nonprovisional U.S. application Ser. No. 14/688,186 filed Apr. 16, 2015, which is a continuation-in-part of nonprovisional U.S. application Ser. No. 14/562,650 filed Dec. 5, 2014, which claims priority to Provisional U.S. Application No. 61/912,205 filed on Dec. 5, 2013 and Provisional U.S. Application No. 62/088,528 filed on Dec. 5, 2014, which are hereby incorporated by reference in its entirety.

FIELD

The present disclosure generally relates to dietary supplements providing phospholipid-docosahexanoic acid and B Vitamins.

BACKGROUND

Polyunsaturated fatty acids have numerous crucial biological functions in mammals. Moreover, in adult humans, certain polyunsaturated fatty acids have been linked to potentially promoting improved cognitive ability and have been theorized as potential treatments for arthritis, cancer, diabetes, kidney disease, and diabetic peripheral neuropathy. Also, certain polyunsaturated fatty acids have been linked to promoting retinal and brain development in fetuses and newborns.

SUMMARY

A manufactured dietary supplement contains a phospholipid extract derived from eggs and the extract contains two forms of phospholipid-docosahexanoic acid derived from eggs. One form of phospholipid-docosahexanoic acid is phosphatidylcholine-docosahexanoic acid, and another form of phospholipid-docosahexanoic acid is phosphatidylethanolamine-docosahexanoic acid. And the phospholipid extract has less than about 3% by weight of free triglycerides. The manufactured dietary supplement also contains L-methylfolate, vitamin $B_6$ and vitamin $B_{12}$.

DESCRIPTION OF THE FIGURES

These and other features, aspects and advantages of the present disclosure are better understood when the following detailed description of the disclosure is read with reference to the accompanying drawing, in which.

DETAILED DESCRIPTION

Figure 1:
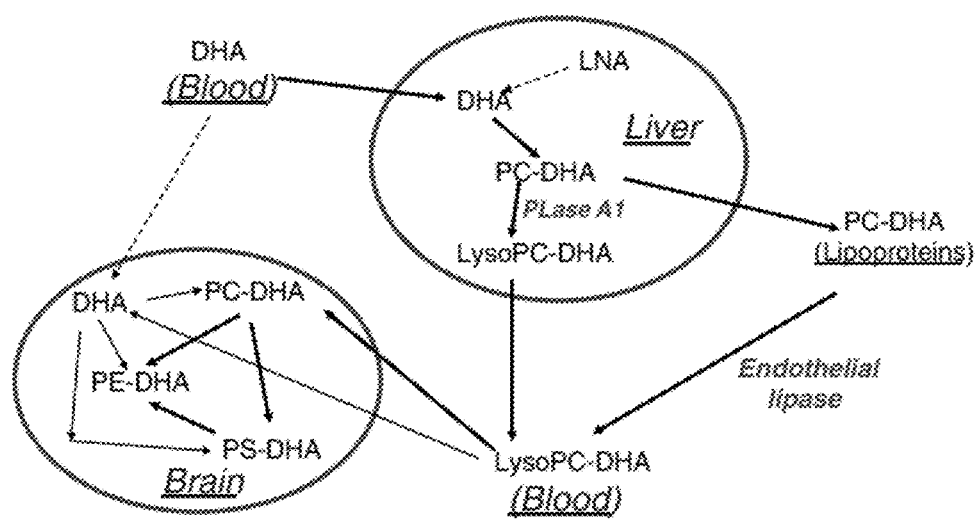
FIG. 1 is a schematic depiction of docosahexanoic acid metabolism in a subject.

Before the present compounds, compositions, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a microparticle" includes one or more microparticles.

"Optional" or "optionally" means that the subsequently described event or circumstance may or may not occur, and that the description includes instances where the event or circumstance occurs and instances where it does not.

As used herein, the term "dietary supplement" does not speak to the regulatory status of one of the embodiments. For example, some embodiments may be regarded by the FDA as a dietary supplement, in other embodiments the FDA may regard the embodiment as a medical food, and in some embodiments the FDA may regard the embodiment as a drug.

As used herein, "subject" refers to a mammal, including a human that is in need of supplementation and/or benefits from the compositions and methods described herein.

As used herein, "organic" refers to a food that complies with U.S.D.A regulations set out herein below.

As used herein, the term "rounded" means that an outer periphery of a structure is substantially free of angularity. For example, the outer periphery of microparticles can have spherical shapes and oval shapes that are free of angularity and have rounded shapes.

As used herein, the term "about" is used to provide flexibility to a numerical range endpoint by providing that a given value may be "slightly above" or "slightly below" the endpoint without affecting the desired result.

The disclosure provides various teachings on dietary supplements containing phospholipid extracts derived from eggs. The ingredients, compounds, chemicals that make up the elements of the dietary supplements may contain vitamins, foods, or other organic matter that is prone to degradation after formulation in a finished dietary supplement. It is common practice to formulate a dietary supplement to include an "overage" or an additional amount of ingredient. Any amount of ingredient, compound, or chemicals that is within an "overage" of the ranges and amounts claimed and exemplified in this disclosure would be considered equivalent.

The disclosure provides dietary supplement that contains a phospholipid extract that may be made up of different forms of phospholipids in different ratios and amounts. Where the disclosure refers to an amount of a specific phospholipid, it is measured by weight and not by molar amount. Where a phospholipid extract refers to a ratio between different phospholipids, it is measured by weight and not by molar amount.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

The nutritional compositions, dietary or nutritional supplements, and methods described herein can comprise, consist of, or consist essentially of the essential elements and limitations described herein, as well as any additional or optional ingredients, components, or limitations described herein or otherwise useful in nutritional formula applications.

The present nutritional compositions, dietary supplements, and methods will now be described more fully hereinafter with reference to the accompanying drawings in which exemplary embodiments of the disclosure are shown. However, these compositions and methods may be embodied in many different forms and should not be construed as limited to the representative embodiments set forth herein. The exemplary embodiments are provided so that this disclosure will be both thorough and complete, and will fully convey the scope of the disclosure and enable one of ordinary skill in the art to make, use, and practice the teachings of the present disclosure.

Polyunsaturated fatty acids have numerous crucial biological functions in mammals. For example, in humans, numerous polyunsaturated fatty acids have been linked to cell membrane synthesis, metabolism, and maintenance. Moreover, in adult humans, certain polyunsaturated fatty acids have been linked to potentially promoting improved cognitive ability and have been theorized as potential treatments for arthritis, cancer, diabetes, lupus, and psoriasis. Also, certain polyunsaturated fatty acids have been linked to promoting retinal and brain development in fetuses and newborns.

For example, docosahexanoic acid ("DHA") is one such polyunsaturated fatty acid that has been implicated in playing a role in fetus and newborn development as well as potentially playing a role in maintaining and/or promoting improved human cognitive ability. DHA is a long chain Omega-3 fatty acid derived from alpha-linolenic acid having double bonds at its 4, 7, 10, 13, 16, and 19 positions. In humans, DHA is primarily found in the brain's grey matter where it functions as a building block for membrane glycerophospholipids. In the brain, DHA is a crucial fatty acid in the cell membrane phospholipids of neuronal synapses and metabolizes to form critical anti-inflammatory agents such as resolvins and protectins.

Although polyunsaturated fatty acids such as DHA are known to play an important role in human cognitive ability, fetus development, and newborn development, Western diets are often deficient in adequate amounts of these polyunsaturated fatty acids, and individuals often resort to polyunsaturated fatty acid supplementation to obtain adequate nutritional amounts of these polyunsaturated fatty acids to potentially avoid problems associated with polyunsaturated fatty acid deficiencies Dietary deficiencies of DHA in particular are associated with a variety of diseases and disorders such as cognitive impairment, infertility (e.g. low sperm motility), impaired fetal brain development, decreased visual acuity, and affective disorders including but not limited to depression. For these and other reasons, pregnant women and health conscious individuals often supplement their diets with fish oil and algae extracts in an attempt to obtain adequate amounts of polyunsaturated fatty acids. Moreover, infant formulas are often supplemented with polyunsaturated fatty acids derived from either of these sources.

In recent years, DHA was discovered to be the precursor to a critical signaling molecule called neuroprotectin-1. It is produced in response to oxidative stress, and has been found in astrocytes, neurons, peripheral blood and lung tissue. Neuroprotectin-1 induces nerve regeneration, reduces the spread of leukocytes, and reduces pro-apoptotic and pro-inflammatory signals, for example during the course of aging.

Peripheral neuropathy affects as many as 62% or more of persons with diabetes and the proportion increases with age. Symptoms include but are not limited to loss of sensation in extremities, muscle weakness, and loss of balance or coordination. Studies in mice found that those fed a diet rich in DHA had higher levels of brain-derived neurotrophic factor, which are hypothesized to promote the long-term maintenance of shape, function, and plasticity of neurons. Diabetic peripheral neuropathy manifests as axonal degeneration, and treatment with DHA has been shown to prevent decreases in blood flow and nerve conduction velocity in rat models with diabetes.

Because it changes the permeability, fluidity, and protein activity of cell membranes, DHA plays a major role in increasing the permeability of cancer cells making them more susceptible to immunological and chemotherapeutic treatments; DHA metabolites may attenuate platelet aggregation, and furthermore may reduce inflammatory processes in neural tissues including brain. The greatest evidence of the neuroprotective effect of DHA has been reported in patients with Alzheimer's disease.

Although fish oil and algae extracts may be a source of polyunsaturated fatty acids, numerous problems exist. For example, fish oil often has an undesirable smell and taste. Due to this problem, numerous fish oil formulations often include taste and smell masking agents. However, most taste and smell masking agents never completely mask the "fishy" taste and smell of these oils. Moreover, these taste and smell masking agents increase production costs and the amount of time required to manufacture formulations having fish oil extracts. Thus, in many regards, fish oil supplementation and production of supplements having these substances remains undesirable due to these problems. Additionally, fish oil and algal oil extracts do not have high quantities of DHA in the phospholipid form. And fish oil extracts also contain higher levels of triglycerides and free fatty acids. The oxidation due to the higher levels of triglycerides and free fatty acids are one of the reasons for the undesirable smell and taste.

In addition, numerous problems exist for DHA derived from these sources and other commonly used forms of DHA. For example, DHA derived from fish oil and algae are primarily covalently bonded to triglycerides, and other types of pharmaceutical grade DHA are ethyl ester forms of DHA, which is not the bioactive form of DHA in the human body. In humans, DHA supplementation in the form of DHA as an ethyl ester or free fatty acid, or triglycerides require multiple steps of metabolic processing to be useful for certain biological functions. Thus, these forms of DHA are energetically disfavored due to the amount of metabolic processing required by a subject's body.

Furthermore, when included in dietary supplements and formulations, the oxidation of DHA in ethyl ester or free fatty acid form, or triglyceride form leads to instability, decreased efficacy, decreased potency, and potentially increased toxicity. The oxidation is also what contributes to the "fishy smell." In addition to the problems mentioned above, the triglyceride and ethyl ester forms of DHA often cause gastrointestinal problems. Therefore, triglyceride and ethyl ester forms of DHA are often enterically coated in an attempt to reduce DHA oxidation and gastrointestinal problems associated with these forms of DHA, which further increases production costs and the time required to manufacture dietary supplements having these substances.

DHA from algae or fish oxidizes (stinks) because it must be broken down to free fatty acid or ethyl ester DHA, which is then transported via albumin into the blood but then the supplement must provide high dosages of DHA to "force" it or push it into blood-brain-barrier ("BBB") or must be converted in the liver to lipid form DHA (only a small amount do this). It takes a high dosages of docosahexanoic acid in free fatty acid or ethyl ester form and triglyceride form to cross the blood brain barrier, which is why dietary supplements contain so much. Ultimately, the DHA must be metabolized into phospholipid-docosahexanoic acid (PL-DHA) in order to be circulating and then go into the BBB. PL-DHA is the only form that can cross the BBB in significant numbers.

Therefore, it is an object of the disclosure to provide nutritional compositions and dietary supplements including a stable source of DHA that avoids or reduces the problems associated with conventional polyunsaturated fatty acid supplementation. The forms of DHA that are most beneficial for nutritional supplementation for cognitive functions are in the phospholipid form, namely phosphatidylcholine docosahexanoic acid ("PC-DHA"), phosphatidylethanolamine docosahexanoic acid ("PE-DHA"), and phosphatidylserine docosahexanoic acid ("PS-DHA"). These phospholipids are conjugated to a docosahexanoic acid (PL-DHA), a tryglyceride with one other R group, where the R group contains a fatty acid. Both PC-DHA and PS-DHA are biosynthesis precursors for phosphatidylserine in the human body, which is important in a number of cell signaling events and critical for long-term survival of neuronal cells.

Described herein are nutritional compositions and dietary supplements containing phospholipids and PL-DHA derived from eggs and methods of making such nutritional compositions and dietary supplements. These nutritional compositions and dietary supplements can be administered to a subject to promote numerous health benefits, which include, but are not limited to, promoting improved cognitive ability, retinal health, decrease inflammation, and neuronal health. Furthermore, these nutritional compositions can be administered to pregnant women and/or newborns to further promote brain and retinal development in fetuses and newborn children.

Eggs contain many phospholipids and the amount of phospholipids in eggs may be increased by supplementing the hens diet with polyunsaturated fatty acids, particularly Omega-3 oils. Eggs contain various Omega-3 fatty acids. Some of the phopholipids contained in eggs include: phosphatidylcholine, phosphatidylethanolamine, phosphatidylserine, lysophosphatidyl choline, sphingomyelin, lysophosphtidyl ethanolamine, and combinations thereof. While fish, algae, and krill are common sources for DHA supplementation, eggs is not a common source for DHA supplementation due to the smaller amounts of DHA available compared to the other sources.

Various phospholipids may be extracted from eggs. This "phospholipid extract" derived from eggs may also be referred to as the raw material or ingredient for a dietary supplement. Reference to phospholipid extracts claimed by this disclosure will always be phospholipid extracts derived from eggs. The phospholipids contained in the phospholipid extract include phospholipid-docosahexanoic acid (PL-DHA) and other phospholipids. Specifically, the PL-DHA of this disclosure may be PC-DHA and/or PE-DHA.

The phospholipid extract may also have some free fatty acids and triglycerides, however, the phospholipid extract should preferably have a small amount triglycerides and free fatty acids. For the purposes of this disclosure, a "free fatty acid" is a fatty acid that is not covalently bonded to a glycerol backbone or is an ethyl ester form of DHA. A "triglyceride" lacks the phosphate group on the third carbon of the glycerol backbone, which also prevents choline, ethanolamine, serine, and inositol from binding to the triglyceride and making it a phospholipid.

Phospholipids (PLs) are found in all animal and plant cell membranes, arranged as lipid bilayers, and when consumed through diet are almost completely absorbed in the intestine. These dietary PLs deliver fatty acids for incorporation into cellular membranes, thereby altering the membrane composition of the cells. As a consequence, cell functions such as signaling, transport, and regulation of membrane-bound enzymes can be modulated by these PLs and thus contribute to health benefits such as regulating inflammatory reaction, blood lipid profiles, cardiovascular risks, neurological development and disorders, immunological function, and liver diseases.

The phospholipid extract or raw material may also contain phosphatidylcholine, phosphatidylethanolamine, phosphatidylserine, lysophosphatidyl choline, sphingomyelin, lysophosphtidyl ethanolamine, and combinations thereof. In one embodiment, the phospholipid extract has less than 5% triglycerides, in another embodiment, the phospholipid extract has less than 3% triglycerides. In one embodiment, the phospholipid extract has less than 0.5% free fatty acids, in another embodiment, the phospholipid extract has less than 0.2% free fatty acids.

The phospholipid extract may sometimes be semi-solid and sticky. It can be difficult to use in tablet or hard capsule products. The raw material is often not soluble in oil, and using the material may be impractical in use in softgel, as it may stick on the mill surface during grinding.

In certain aspects, these nutritional compositions and dietary supplements include a body that encapsulates iron, folate, and an additive, wherein the additive can include microparticles. In certain aspects, the microparticles have a substantially rounded shape and include a core. The core contains the raw material or phospholipid extract, which effectively and efficiently delivers the phospholipid extract to the subject. The core of the microparticle may be coated. These microparticles can be incorporated into the nutritional composition to improve efficacy of phospholipid delivery.

In addition, these microparticles can be made by providing a microparticle core made from a pharmaceutically acceptable material and a or phospholipid extract, then coating the microparticle core with a first layer, and drying the coated microparticle core, thereby forming the microparticle for the nutritional composition.

In other aspects the dietary supplement contains the phospholipid extract without the use of microparticles. These may include extract in the form of micelles or nanomicelles.

Additional features, aspects and advantages of the disclosure will be set forth in the detailed description which follows, and in part will be readily apparent to those skilled in the art from that description or recognized by practicing the teachings of the disclosure as described herein. It is to be understood that both the foregoing general description and the following detailed description present various embodiments of the disclosure, and are intended to provide an overview or framework for understanding the nature and character of the disclosure as it is claimed. The accompanying drawings are included to provide a further understanding of the disclosure, and are incorporated in and constitute a part of this specification.

Nutritional Compositions

Described herein are nutritional compositions that include a body encapsulating iron, folate, and an additive, wherein the additive includes a microparticle having a core that includes a phospholipid extract and a coating. The body in the nutritional compositions described herein can include, but is not limited to, a tablet, an enteric coated tablet, a capsule, an enteric coated capsule, a softgel capsule, or an enteric coated softgel capsule encapsulating iron, folate, and the additives, for example the microparticles, described herein.

Docosahexanoic Acid (DHA)

The nutritional compositions and dietary supplements described herein include a pharmaceutically acceptable phospholipid-DHA derived from eggs and more preferably include organic DHA or DHA derived from organic eggs.

The docosahexanoic acid described herein generally includes the following formula:

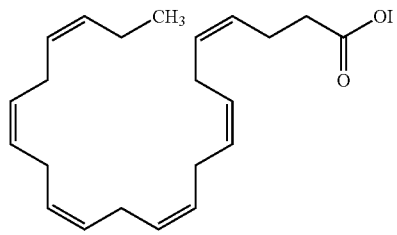

In certain aspects, the PL-DHA can include a phospholipid that is preferably covalently bonded either directly to the DHA or indirectly (via a saturated or unsaturated lower alkyl linker having $C_1$-$C_8$) to the DHA. The phospholipid will have a glycerol backbone, an $R_1$ group on the first carboxyl group, and $R_2$ on the second carboxyl group, and a phosphate group on the third carboxyl group. For example, the phospholipid can include phosphatidylcholine, phosphatidylethanolamine, phosphatidylserine, or combinations thereof. In certain aspects, the $R_1$ is a fatty acid. In certain aspects, the $R_2$ is a DHA.

The phosphate group of the phospholipid can include a primary amine group, a secondary amine group, a tertiary amine group, a trimethyl amine group, or a combination thereof, and $R_1$ can include a hydrogen, a hydroxyl group, a saturated or unsaturated alkyl group, an alkoxy group, an omega-3 fatty acid, or any combination thereof. In certain aspects, the phosphate group will be bound to $NH_3^+$ or $N(CH_3)_3$.

In certain aspects, PL-DHA of the nutritional composition may include 1-palmitoyl-2-docosahexaenoyl-sn-glycero-3-phosphocholine or 1-hexadecanoyl-2-(4Z,7Z,10Z,13Z,16Z,19Z-docosahexaenoyl)-sn-glycero-3-phosphocholine or phosphatidylcholine-docosahexanoic acid ("PC-DHA"), 1-stearoyl-2-docosahexaenoyl-sn-glycero-3-phosphoethanolamine or 1-octadecanoyl-2-(4Z,7Z,10Z,13Z,16Z,19Z-docosahexaenoyl)-sn-glycero-3-phosphoethanolamine or phosphatidylethanolamine-docosahexanoic acid ("PE-DHA"), or combinations thereof. For example, Formula 1 depicts one representative example of PC-DHA.

Formula 1

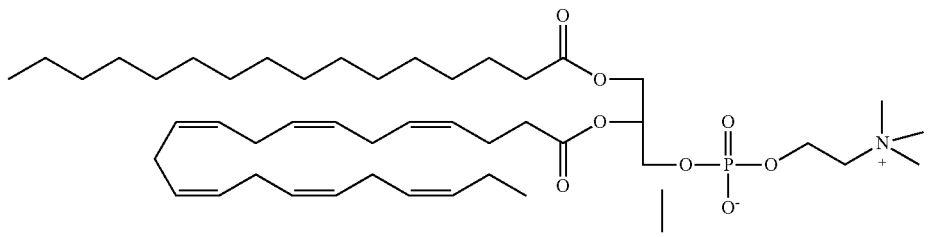

The DHA shown in Formula 1 above is preferred over fish oil and algae derived forms of DHA for human nutrition because this DHA is in the phospholipid form, which aid in docosahexanoic stability and potency. Furthermore, these forms of DHA are more palatable to subjects than those derived from fish oil and algae extracts. Without wishing to be bound by theory, it is thought that these forms of DHA are more easily metabolized by a subject and more easily cross the blood brain barrier.

FIG. 1 further illustrates this concept. For example, as shown in FIG. 1, linolenic acid (i.e., "LNA") and most forms of docosahexanoic acid are metabolized in the liver in order to cross the blood brain barrier before being used in various metabolic functions in the brain. For example, linolenic acid is converted into DHA, and DHA is further bonded to phosphatidylcholine to generate PC-DHA. After synthesizing PC-DHA, liver phospholipase A1 (PLase A1) hydrolyzes PC-DHA to form LysoPC-DHA, which can subsequently pass the blood brain barrier and can be used in various metabolic functions in the brain such as maintaining neuronal membrane glycerophospholipids and potentially preventing or reducing apoptosis of glial cells and neurons. As also shown in FIG. 1, if free PC-DHA is present, endothelial lipase can also hydrolyze this free PC-DHA to form LysoPC-DHA, which can also subsequently pass the blood brain barrier and be used in various metabolic functions in the brain such as maintaining neuronal membrane glycerophospholipids and potentially preventing or reducing apoptosis glial cells and neurons.

Figure 2:
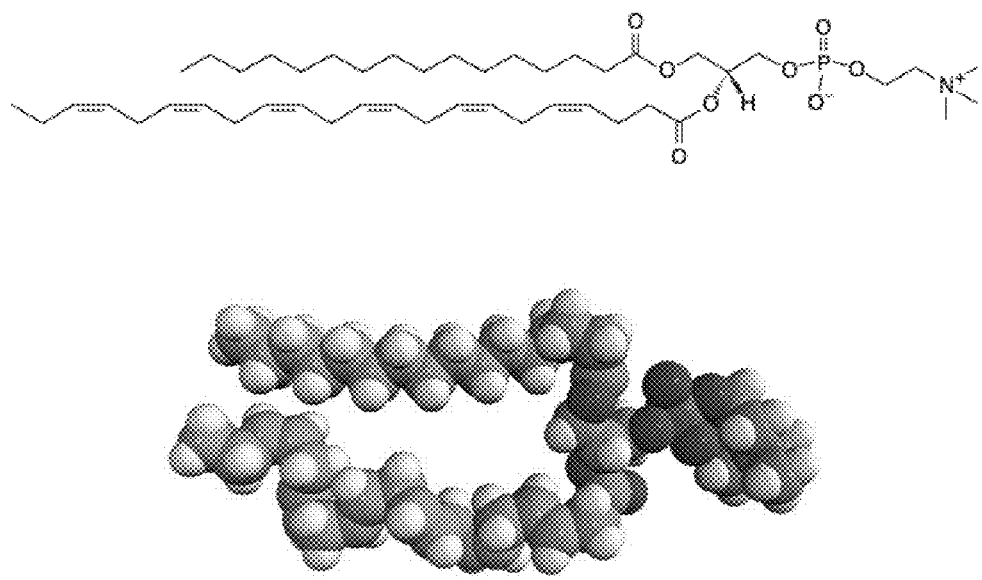
FIG. 2 is a schematic depiction of phosphatidylcholine-docosahexanoic acid.

FIG. 2 is an illustration of PC-DHA.

Figure 3:
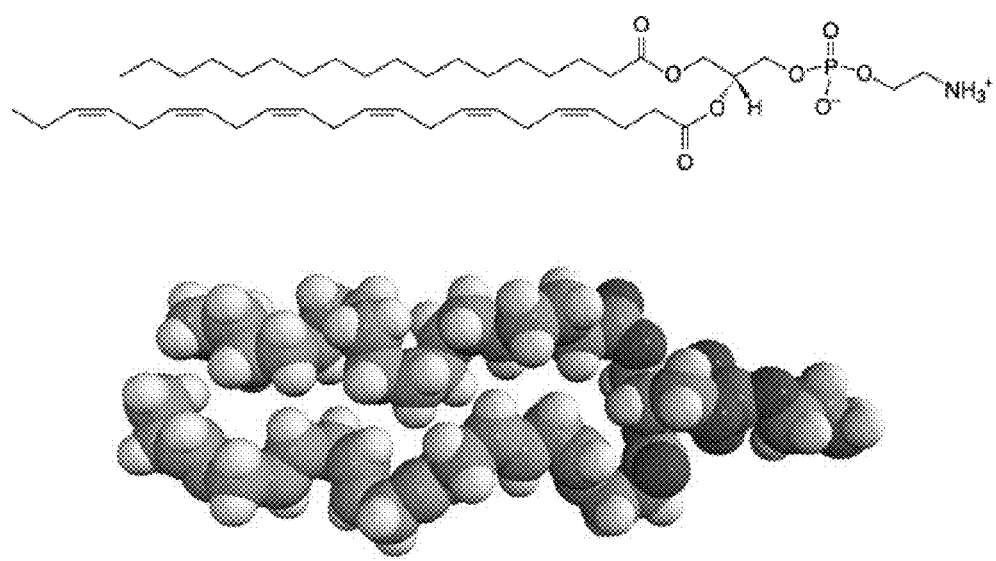
FIG. 3 is a schematic depiction of phosphatidylethanolamine-docosahexanoic acid.

FIG. 3 is an illustration of PE-DHA.

The biochemical pathways that result in DHA conjugated to the phospholipid usually result in the DHA molecule binding to the number one carboxyl group of the glycerol backbone. Though it is possible however rare that the DHA may naturally be covalently bonded to the first carboxyl group. The many double carbon bonds of the DHA fatty acid cause the DHA fatty acid to be at an angle in relation to the glycerol backbone, as opposed to a saturated fatty acid that will position itself more at a ninety degree angle to the glycerol backbone. Due to this to spatial configuration it is extremely rare for phopholipids to have two DHA fatty acids conjugated to both the one carbon and the two carbon positions, but it does occur in nature.

Krill oil is known to be a source of phospholipid and DHA nutritional supplementation, however, krill oil also contains significant amounts of eicosapentaenoic acid (EPA).

Phospholipids extracts derived from eggs are also preferential in that egg yolk does not naturally contain eicosapentaenoic acid (EPA), but does contain arachidonic acid (AA). EPA interferes with the body's use of AA and since EPA is a precursor to DHA that requires additional metabolic work for use by humans, it is not preferred for human Omega-3 fatty acid needs. EPA is not used in human brain maintenance as DHA has been shown to function. Not all biochemical pathways are perfect and some EPA may exist in nature in phospholipid extracts from eggs, however the amount would be small. In one embodiment, the phospholipid extract comprises less than 1.5% EPA by weight. In one embodiment, the phospholipid extract comprises less than 1% EPA by weight. In one embodiment, the phospholipid extract comprises less than 0.5% EPA by weight.

DHA and AA are fatty acids that are needed by young children, pregnant and lactating women, and people with degenerative diseases involving oxidative stress, especially those of the nervous system such as Alzheimer's and acute or chronic peripheral neuropathy.

When DHA is covalently linked to phosphatidylethanolamine, this form of DHA can be easily converted to DHA forms that can cross the blood brain barrier. For example, without wishing to be bound by theory, PE-DHA can be converted into LysoPC-DHA by various metabolic processes and eventually cross the blood brain barrier.

In addition to crossing the blood brain barrier, PC-DHA and PE-DHA can be used as a polyunsaturated fatty acid nutritional source that crosses the placental barrier in pregnant mothers and provides a fetus with sufficient DHA amounts for adequate brain, nervous system, and retinal development.

In contrast to the PC-DHA and PE-DHA derived from eggs discussed above, DHA derived from fish oil and algae are primarily covalently bonded to triglycerides that do not include phosphate groups and/or phospholipids. Furthermore, the DHA derived from fish oil and algae often require far more metabolic steps to be converted into a useful form of DHA that can cross the blood brain barrier and/or the placental barrier.

In certain aspects, the phospholipid extract includes PC-DHA and PE-DHA. In this aspect, the combination of PC-DHA and PE-DHA provided in a microparticle or a dietary supplement can be 10% to 40% (by weight) of the overall amount of phospholipid extract in the dietary supplement. In one aspect, PC-DHA can be 40% to 95% of the overall amount of PL-DHA in the dietary supplement, and PE-DHA can be 5% to 60% of the overall amount of DHA in the dietary supplement. The PC-DHA and PE-DHA may also be used in a dietary supplement without the microencapsulation. In one aspect, at least 5% of the phospholipid extract, by weight, is PC-DHA. And in another aspect, at least 5% the phospholipid extract, by weight, is PE-DHA. In one aspect, from between about 9% and about 15% of the phospholipid extract, by weight, is PC-DHA. In one aspect, from between about 9% and about 15% of the phospholipid extract, by weight, is PE-DHA.

Preferably the amount of triglycerides is low. In one aspect, the amount of triglycerides is less than 5% of the phospholipid extract, and in another aspect the amount of triglycerides is less than 3% of the phospholipid extract.

In certain aspects, the DHA described herein includes a ratio of PC-DHA to PE-DHA ranging from 20:1 to 1:1. In another embodiment, the DHA described herein includes a ratio of PC-DHA to PE-DHA ranging from 5:1. In another embodiment, the DHA described herein includes a ratio of PC-DHA to PE-DHA ranging from 1:1.

In certain aspects the phospholipid extract will be substantially free or completely free of phosphatidylserine. In certain aspects the phospholipid extract will be substantially free or completely free of eicosapentaenoic acid.

DHA from Eggs

Eggs naturally contain a relatively high about of phospholipids and phospholipid conjugated DHA (PL-DHA). Additionally, to increase the amount of phospholipids and PL-DHA in eggs, chicken feed may be supplemented with a source of Omega-3 fatty acids like flax seeds, or other sources high in Omega-3 fatty acids. Between 200 mg to 300 mg of usable phospholipid extract for nutritional supplementation can be extracted from one egg.

Omega-3 fatty acid enriched eggs have been shown to have 39% less AA than non-enriched eggs, a non-essential (sometimes inflammatory) Omega-6 fatty acid that most people get ample amounts of in their diet. It has also been shown that Omega-3 fatty acid enriched eggs had 5 times as much Omega-3 fatty acid as conventional eggs.

Hens that are fed organic chicken feed potentially will be able to produce DHA, including PC-DHA to PE-DHA, derived from eggs that may be labeled as a source of Organic DHA.

In certain aspects and as discussed further below, the PL-DHA is only included in the microparticles of the nutritional composition. In other aspects, a portion of the phospholipid extract or PL-DHA can be included in the microparticles and another portion of the phospholipid extract or PL-DHA can be included in a portion of the encapsulating body (e.g., tablets, softgels, capsules, or chewable) that is not the microparticle. For example, 90%, 85%, 80%, 75%, 70%, 65%, 60%, 55%, or 50% of the overall amount of the phospholipid extract or PL-DHA can be in the microparticles and the remainder of DHA can included in a portion of the encapsulating body that is not the microparticle.

The dietary supplement of the present disclosure may provide a phospholipid extract to be formulated with other vitamins and minerals in the form of a tablet, softgel, capsule, chewable, or gummy. The phospholipid extract may be provided in a dietary supplement in the amount ranging from 20 mg to 1500 mg, 100 mg to 900 mg, 100 mg to 800 mg, 100 mg to 700 mg, 100 mg to 600 mg, 100 mg to 500 mg, 100 mg to 400 mg, 100 mg to 300 mg, 100 mg to 200 mg, 200 mg to 800 mg, 200 mg to 650 mg, 200 mg to 500 mg, 200 mg to 450 mg, 200 mg to 300 mg, 300 mg to 750 mg, 300 mg to 600 mg, 300 mg to 500 mg, 300 mg to 450 mg, 300 mg to 400 mg, 400 mg to 650 mg, 400 mg to 600 mg, 400 mg to 550 mg, 400 mg to 500 mg, 400 mg to 450 mg, or any range having endpoints falling within any of the preceding ranges. In one embodiments, the dietary supplement contains 200 mg of the phospholipid extract. In one embodiments, the dietary supplement contains 100 mg of the phospholipid extract. In one embodiments, the dietary supplement contains 250 mg of the phospholipid extract.

The PC-DHA may be provided in a dietary supplement in the amount ranging from 1 mg to 150 mg, 1 mg to 90 mg, 1 mg to 80 mg, 10 mg to 70 mg, 10 mg to 60 mg, 10 mg to 50 mg, 10 mg to 40 mg, 10 mg to 30 mg, 10 mg to 20 mg, 20 mg to 80 mg, 20 mg to 65 mg, 20 mg to 50 mg, 20 mg to 45 mg, 20 mg to 30 mg, 30 mg to 75 mg, 30 mg to 60 mg, 30 mg to 50 mg, 30 mg to 45 mg, 30 mg to 40 mg, 40 mg to 65 mg, 40 mg to 60 mg, 40 mg to 55 mg, 40 mg to 50 mg, 40 mg to 45 mg, 10 mg to 20 mg, or any range having endpoints falling within any of the preceding ranges. In one embodiments, the dietary supplement contains about 10 mg of PC-DHA. In one embodiments, the dietary supplement contains about 20 mg of the PC-DHA. In one embodiments, the dietary supplement contains about 25 mg of the PC-DHA.

The PE-DHA may be provided in a dietary supplement in the amount ranging from 1 mg to 150 mg, 1 mg to 90 mg, 1 mg to 80 mg, 10 mg to 70 mg, 10 mg to 60 mg, 10 mg to 50 mg, 10 mg to 40 mg, 10 mg to 30 mg, 10 mg to 20 mg, 20 mg to 80 mg, 20 mg to 65 mg, 20 mg to 50 mg, 20 mg to 45 mg, 20 mg to 30 mg, 30 mg to 75 mg, 30 mg to 60 mg, 30 mg to 50 mg, 30 mg to 45 mg, 30 mg to 40 mg, 40 mg to 65 mg, 40 mg to 60 mg, 40 mg to 55 mg, 40 mg to 50 mg, 40 mg to 45 mg, 10 mg to 20 mg, or any range having endpoints falling within any of the preceding ranges. In one embodiments, the dietary supplement contains about 10 mg of PE-DHA. In one embodiments, the dietary supplement contains about 20 mg of the PE-DHA. In one embodiments, the dietary supplement contains about 25 mg of the PE-DHA.

The PL-DHA may be provided in a dietary supplement in the amount ranging from 2 mg to 300 mg, 2 mg to 180 mg, 2 mg to 160 mg, 20 mg to 140 mg, 20 mg to 120 mg, 20 mg to 100 mg, 20 mg to 80 mg, 20 mg to 60 mg, 20 mg to 40 mg, 40 mg to 160 mg, 40 mg to 130 mg, 40 mg to 100 mg, 40 mg to 90 mg, 40 mg to 60 mg, 60 mg to 150 mg, 60 mg to 120 mg, 60 mg to 100 mg, 60 mg to 90 mg, 60 mg to 80 mg, 80 mg to 130 mg, 80 mg to 120 mg, 80 mg to 110 mg, 80 mg to 100 mg, 80 mg to 90 mg, 40 mg to 80 mg, or any range having endpoints falling within any of the preceding ranges. In one embodiments, the dietary supplement contains about 20 mg of PL-DHA. In one embodiments, the dietary supplement contains about 40 mg of the PL-DHA. In one embodiments, the dietary supplement contains about 50 mg of the PL-DHA.

Microparticles

Microparticles can be included in the disclosed nutritional compositions, and more specifically, the microparticles described herein are preferably included within a tablet, an enteric coated tablet, a capsule, an enteric coated capsule, a softgel capsule, or an enteric coated softgel capsule.

The microparticles described herein generally include a microparticle core and a layer or a plurality of layers coated on an outermost surface of the microparticle core. The microparticle core is preferably made from a pharmaceutically acceptable material that includes, but is not limited to, tartaric acid, sugar, calcium carbonate, mannitol, microcrystalline cellulose, silica, starch or any combination thereof. These materials are mixed with the phospholipid extract. The phospholipid extract may include PC-DHA, PE-DHA, or a mixture. PL-DHA and other Omega-3 fatty acids may also be incorporated in the microparticle core.

It is preferable that the microparticle cores have a substantially rounded shape such that the microparticle cores do not aggregate during the production of the microparticles. In addition, because non-rounded shaped microparticle cores tend to aggregate and slow the production process, it is preferable that the microparticle cores have a rounded shape to facilitate production of rounded microparticles.

The microparticle cores described herein can be generally produced with any known extrusion and spheronization techniques that can obtain the desired microparticle diameters described below. For example, the microparticle core material can be subjected to radial extruding process, axial extruding process, cone extruding process, dome extruding process, die roller extruding process, or basket extruding process. These materials can be generally extruded through a die or mesh having variable sizes. For example, the die and mesh sizes associated with these extruding techniques can include 200 μm to 8000 μm, 300 μm to 7500 μm, 300 μm to 4000 μm, 300 μm to 2000 μm, 400 μm to 2000 μm, 400 μm to 1000 μm, and 500 μm to 800 μm to produce microparticle cores having a desired particle diameter. After extrusion, the microparticle core materials can be further subjected to any known spheronization treatment to further ensure sufficient microparticle core roundness.

In certain aspects, the microparticle cores can be further subjected to flow cytometry and separated based on desired microparticle core roundness. For example, in certain aspects, the desired microparticle core diameter ranges from 180 μm to 425 μm. In exemplary embodiments, the microparticles may have an accumulated volume average particle diameter D50 of from approximately 250 μm to approximately 425 μm to meet 40-60 mesh requirements. Or the microparticles may have an accumulated volume average particle diameter D70 of from approximately 180 μm to approximately 250 μm to meet 60-80 mesh requirements. Or the microparticles may have an accumulated volume average particle diameter D90 of from approximately 150 μm to approximately 180 μm to meet 80-100 mesh requirements.

In an exemplary embodiment, the microparticle cores may have a volume average particle size distribution index GSDv of approximately 1.30 or less. When GSDv is approximately 1.30 or less, little microparticle core aggregation occurs and sufficient microparticle roundness can be obtained.

The accumulated volume average particle diameter D50 and the average particle size distribution index of the microparticle cores may be measured, for example, in the following manner. Based on a particle size distribution measured with such a measuring device as Coulter Counter TA II (available from Beckman Coulter, Inc.) or Multisizer II (available from Beckman Coulter, Inc.), accumulated distributions of volume and number are each drawn from the small diameter side with respect to the divided particle size ranges. The particle diameters where the accumulated value is 16% are designated as volume $D_{16V}$ and number $D_{16P}$, the particle diameters where the accumulated value is 50% are designated as volume $D_{50V}$ and number $D_{50P}$, and the particle diameters where the accumulated value is 84% are designated as volume $D_{84V}$ and number $D_{84P}$. By using these values, the volume average particle size distribution index (GSDv) is calculated as $(D_{84V}/D_{16V})^{1/2}$ and the number average particle size distribution index (GSDp) is calculated as $(D_{84P}/D_{16P})^{1/2}$. The microparticles may have a shape factor SF1 of from approximately 110 to approximately 140, and preferably from approximately 120 to approximately 140, which results in microparticle cores having little shape irregularity and having sufficient roundness (e.g., spherical shape).

SF1 is a shape factor that shows the extent of unevenness on the surface of the microparticle cores, and is calculated as follows. An optical micrograph of the microparticle cores scattered on a glass slide is acquired to a Luzex image analyzer through a video cam, and SF1 is calculated according to the following expression from the value obtained by dividing square of the maximum length of the toner particles by the projected area (($ML)^2/A$) for 50 toner particles, and the average value thereof is designated as SF1.

$$SF1=(ML)^2/a \times \pi/4 \times 100$$

wherein ML represents the maximum length of the toner particles, and A represents the projected area of the particles.

After obtaining microparticle cores having desirable roundness and diameter, the microparticle cores are then subjected to a coating process in which one or more coating layers are coated on an outermost surface of the microparticle cores. For example, in certain aspects, an outermost layer of the microparticle cores are coated with a solution, dispersion, or suspension. In some aspects, the coating may also contain additional DHA derived from eggs described above. In certain aspects, this coating can contain additional components that include, but are not limited to tocopherol and other preservatives, stabilizers, and excipients.

This coating can partially or completely coat the outermost layer of the microparticle core. In certain aspects, it is preferable that the coating completely coats the outermost layer of the microparticle core, and this combination of microparticle core and coating forms the microparticle. Depending on the type of material used for the microparticle core, it may be desirable to form an intermediary layer disposed between the outermost surface of the microparticle core. In one aspect the coating is pH dependant and may be used for targeting the absorption at specific locations in the GI tract. In this aspect, the intermediary layer may reduce or prevent the docosahexanoic acid from interacting and potentially blocking absorption.

In certain aspects, a plurality of coatings can be provided on the microparticle core in order to form the desired microparticle. In this aspect, the microparticle core can be coated with a coating containing phospholipid extract or PL-DHA on the outermost surface of the microparticle core. In certain aspects, this coating is allowed to dry at a desired temperature and for a desired time period. Next, a second coating can be applied. In certain aspects, this second coating can include time release agents and additional excipients to more slowly and controllably administer, for example, the docosahexanoic acid derived from eggs to a subject. These time release coatings are described in greater detail further below. In further embodiments, additional coating layers can be provided on the microparticle cores.

In certain aspects, it is desirable that the microparticles do not exceed 500 μm in diameter because adverse effects such as gastrointestinal irritation may occur. It is also desirable that the microparticles have a substantially uniform shape and particle diameter to ensure efficient delivery to the subject. For example, in certain aspects, the microparticles described herein are monodisperse and have a polydispersity index (PDI) ranging from about 1.5 to 1, from about 1.3 to 1, and more preferably from about 1.2 to 1.

Organic DHA

The National Organic Program (NOP) under the direction of the Agricultural Marketing Service (AMS), an arm of the United States Department of Agriculture (USDA) is a national program that establishes national standards for the production and handling of organically produced products, including a National List of substances approved for and prohibited from use in organic production and handling. NOP is codified in 7 CFR Part 205, which is incorporated by reference herein.

The final regulation declared that "Producers and handlers of agricultural products used as ingredients in cosmetics, body care products, and dietary supplements could be certified as organic operations. The ultimate labeling of cosmetics, body care products, and dietary supplements, however, has yet to be addressed."

The USDA has stated that "There are agricultural products, including personal care products, that, by virtue of their organic agricultural product content, may meet the NOP standards and be labeled as "100 percent organic," "organic" or "made with organic" pursuant to the NOP regulations. Businesses that manufacture and distribute such products may be certified under the NOP, and such products may be labeled as "100 percent organic," "organic" or "made with organic" so long as they meet NOP requirements. Additionally, products that may be labeled "100 percent organic" or "organic" may also carry the USDA organic seal."

Except for exempt and excluded operations, each production or handling operation or specified portion of a production or handling operation that produces or handles crops, livestock, livestock products, or other agricultural products that are intended to be sold, labeled, or represented as "100 percent organic," "organic," or "made with organic (specified ingredients or food group(s))" must be certified. This means that the organic egg farm, the manufacturer of the organic egg phospholipid extract, the intermediate manufacturer, and the final product manufacturer would need to be certified.

A certified operation must only use allowed substances, methods, and ingredients for the production and handling of agricultural products that are sold, labeled, or represented as "100 percent organic," or "organic," for these products to be in compliance with the Act and the NOP regulations. Use of ionizing radiation, sewage sludge, and excluded methods are prohibited in the production and handling of organic agricultural products.

The National List identifies synthetic substances, materials and ingredients that may be used in organic farming and production operations. The list also highlights non-synthetic substances, materials and ingredients that cannot be used. Notably, microcrystalline cellulose and methyl cellulose, which are ubiquitous excipients in dietary supplements, are prohibited ingredients. This limitation clearly affects finished product manufacturers.

Most DHA and Omega fatty acids raw materials used in nutritional and dietary supplements are derived from algae and fish sources. The extraction processes are not processes that are eligible to be certified as "organic." These extraction techniques also tend to be responsible for the increased the amount of free fatty acids/ethyl ester DHA and tryglycerides as compared to the phospholipid extract of this disclosure. Additionally, some algae sources are genetically modified which also prevent products derived from the algae as certified "organic." The present disclosure is the only known source of dietary supplementation of DHA that is able to be certified as "organic" by the USDA.

Organic egg production is the production of eggs through organic means. There are three main requirements for organic egg production:

Poultry can be exposed to antibiotics only during infectious outbreak.

Poultry must be fed organic feed (no animal byproducts or genetically-modified crops).

Poultry must have access to outdoors. It cannot be raised in cages.

Organic production is also regulated by animal welfare audit system. Mistreatment of the chickens could potentially lead a farmer to losing his organic certification.

Requirements of Phospholipid Extract Intermediate Manufacturers

Phospholipid extract intermediate manufacturers would need to be certified as organic operations.

(a) Mechanical or biological methods, including but not limited to cooking, baking, curing, heating, drying, mixing, grinding, churning, separating, distilling, extracting, slaughtering, cutting, fermenting, eviscerating, preserving, dehydrating, freezing, chilling, or otherwise manufacturing, and the packaging, canning, jarring, or otherwise enclosing food in a container may be used to process an organically produced agricultural product for the purpose of retarding spoilage or otherwise preparing the agricultural product for market.

(b) Nonagricultural substances allowed under §205.605 and non-organically produced agricultural products allowed under §205.606 may be used:
  (1) In or on a processed agricultural product intended to be sold, labeled, or represented as "organic," pursuant to §205.301(b), if not commercially available in organic form.
  (2) In or on a processed agricultural product intended to be sold, labeled, or represented as "made with organic (specified ingredients or food group(s))," pursuant to §205.301(c).

(c) The handler of an organic handling operation must not use in or on agricultural products intended to be sold, labeled, or represented as "100 percent organic," "organic," or "made with organic (specified ingredients or food group(s))," or in or on any ingredients labeled as organic:
  (1) Practices prohibited under paragraphs (e) and (f) of §205.105.
  (2) A volatile synthetic solvent or other synthetic processing aid not allowed under §205.605: Except, That, nonorganic ingredients in products labeled "made with organic (specified ingredients or food group(s))" are not subject to this requirement.

In one embodiment, this disclosure provides for phospholipids to be used in a dietary supplement that may be labeled "organic" according to the USDA guidelines. In one embodiment, this disclosure provide for DHA to be used in a dietary supplement that may be labeled "organic" according to the USDA guidelines. In one embodiment, this disclosure provide for PL-DHA to be used in a dietary supplement that may be labeled "organic" according to the USDA guidelines.

Eggs may be farmed following the USDA guidelines for "organic" foods. The phospholipids from the eggs from organically raised and fed hens are then extracted to be "Organic Phospholipid-DHA," "Organic DHA," or "Organic Phospholipids." Then the organic phospholipid extract may be included in a dietary supplement in the form of a tablet, capsule, softgel, chewable tablet/softgel, or gummy.

Folic Acid and Folate

A pharmaceutically acceptable form of folic acid, folic acid derivatives, folate, reduced folate, or any combination thereof is included within the dietary supplement. Folate has been shown to play a broad role in nucleotide synthesis, catecholamine (Dopamine, Norepinephrine, and Serotonin) synthesis, and methylation in mammals. Moreover, folic acid is known to play a role in nucleotide biosynthesis processes, and more specifically in the synthesis of thymine from uracil (i.e., dUMP, deoxyuracil monophosphate). In adult humans, folic acid supplementation has been implicated in reducing megaloblastic anaemia often associated with folate deficiency and/or side effects associated with various medical treatments (e.g., chemotherapy). Women during periconceptual periods, people with alcoholism, irritable bowel syndrome, celiac disease, and depression may benefit from supplements to natural folate due to its critical role in neural development, catecholamine regulation, gene expression, cell division, and blood cell formation.

Folate metabolism leads to the production of key myelin proteins that function to protect axons. Peripheral neuropathy can result from damage or loss of the proteins that make up 30% of the myelin in the peripheral nervous system.

In addition to its role in biosynthesis, folate is important in trans-methylation, which is of broad relevance for human health. Trans-methylation is the process by which DNA, RNA, proteins, lipids, and neurotransmitters are methylated (acquire a methyl group through alkylation) This methyl group assignment regulates the function of for instance genes, (i.e. epigenetics), and myelin basic protein; interruptions in the methylation cycle or deviant distribution of the methyl groups can play an essential role in development of cancer and neuropathy (including paralysis).

Two folate species reduced from folic acid, dihydrofolate and tetrahydrofolate, are not directly involved in the metabolic pathway, but instead transfer one-carbon moieties toward either methylation or DNA synthesis pathways. Methotrexate (a common chemotherapy drug) is a competitive and irreversible inhibitor of the rate limiting enzyme dihydrofolate reductase that converts folic acid to its reduced forms, thereby tightly regulating the folate cycle via feedback and end product inhibition.

One form of reduced folic acid, folinic acid, is incorporated into purine (used by the mammalian body in DNA and RNA synthesis and repair) during biosynthesis. Two of the four bases of DNA, two of the four building blocks of RNA, and a significant component in a suite of important biomolecules are purines. They may also function as neurotransmitters.

The bioavailable form of folate, L-methylfolate or 5-methyltetrahydrofolate, is essential for the synthesis and protection of tetrahydrobiopterin, a rate limiting cofactor in the production of melatonin and central catecholamines: Dopamine, Norepinephrine, and Serotonin. It is also a cofactor in the production of nitric oxide, important in the regulation of blood pressure and blood flow. Endothelial nitric oxide is dependent on tetrahydrobiopterin availability and affects the disease state in individuals with diabetes, artherosclerosis, and hypoxic pulmonary hypertension. Additionally, L-methylfolate also regulates homocysteine metabolism, increased plasma levels of which are a risk factor for vascular disease and pregnancy complications. For these reasons and others, L-methylfolate may be an important supplement in the maintenance and treatment of both mental and vascular health.

In addition, folic acid has been shown to play a role in preventing neural tube defects that occur during pregnancy. For example, although the molecular and physiological mechanisms are currently unknown, folic acid supplementation has been theorized to reduce the occurrence of spina bifida by up to 70%. Thus, for at least these reasons, it is desirable to include a pharmaceutically acceptable form of folic acid and folic acid derivatives in the disclosed dietary supplements.

Various forms of folate are present in high concentrations in eggs. For example, folic acid, reduced folate, dihydrofolate, tetrahydrofolate, 10-formylfolic acid, 5-formyltetrahydrofolate, and 5-methyltetrahydrofolate are present in egg yolks. Therefore, in certain aspects and to potentially lower production costs of the disclosed dietary supplements, it is desirable to extract folate from eggs while obtaining the phospholipid extract.

In certain aspects, folate derivatives having substituents at its $N^5$ or $N^{10}$ position have increased stability and are less prone to cleavage and oxidation. Thus, these folic acid derivatives may be favored in the disclosed dietary supplements. For example, in certain aspects, it is preferable that at least one of folic acid, 10-formyl folic acid, 5-formyl tetrahydrofolate, 5-methyl tetrahydrofolate, or any combination thereof is present at a higher concentration in the nutritional composition than dihydrofolate and tetrahydrofolate, and in certain aspects, dihydrofolate and/or tetrahydrofolate are not present in the dietary supplement.

The total biologically active amount of folate: folic acid and derivatives thereof present in the dietary supplement ranges from 100 μg to 15 mg. Total biologically active amounts of folic acid and derivatives thereof below 100 μg are potentially inadequate to prevent or reduce problems associated with folate deficiencies (e.g., megaloblastic anaemia, neural tube defects in fetuses, etc.). Pregnant mothers are recommended to take between 400 mcg and 1 mg of folate. High dosages of folate have been shown to improve a number of human ailments and conditions including impaired cognitive function, ADHD, memory loss, diabetic peripheral neuropathy, and depression. Therefore, in certain aspects, the total biologically active amount of folate and derivatives thereof present in the dietary supplement from 100 μg to 15 mg, 400 μg to 800 μg, 400 μg to 1000 μg, 800 μg to 1000 μg, 1 mg to 3 mg, 3 mg to 6 mg, 7.5 mg to 15 mg, or any range having endpoints falling within any of the preceding ranges.

In certain aspects, the total amount of folate, folic acid, and reduced folate derivatives present in the nutritional composition ranges from 0.1 mg to 20 mg based on the total weight of the nutritional composition.

Folate may be provided through many different pharmaceutically acceptable salts. For example, L-methylfolate may be in a salt with calcium, magnesium, zinc, or any other ion known in the art. 5-formyl tetrahydrofolate may also be administered in any pharmaceutically acceptable salt.

In certain aspects, the folic acid and folate derivatives are not included in the microparticles of the nutritional composition. In other aspects, a portion of the folic acid and folate derivatives are included in any of the coated layers of the microparticles and another portion of the folic acid and folate derivatives are included in the encapsulating body (e.g., tablets and capsules) that is not the microparticle. For example, in certain aspects, at least 90%, 85%, 80%, 75%, 70%, 65%, 60%, 55%, or 50% of the overall amount of the folic acid and folic acid derivatives are not in the microparticles, and in this aspect, the remainder of the folic acid and folic acid derivatives can included in the microparticle.

Iron

A pharmaceutically acceptable form of iron is also included within the disclosed Iron may be provided through many different pharmaceutically acceptable salts. In the human body, iron is a key component, which is often complexed with various porphyrin rings to facilitate numerous metabolic and biological processes. More specifically, iron is often complexed with heme groups to form hemoglobin, and iron is also often complexed with various cytochromes (e.g., Cytochrome C in the mitochondria) to carry out electron transport during the production of adenosine tri-phosphate (i.e., ATP) in the mitochondria.

In humans, iron deficiency is usually associated with various anemias, thrombocytosis, decreased immunity, increased susceptibility to sepsis, increased maternal mortality, and atrophy of mucous membranes (e.g., Plummer-Vinson syndrome). Furthermore, iron deficiency in pregnant mothers, can potentially lead to low birth weights, preterm birth, and under development in a newborn child. Thus, for at least these reasons, it is desirable to include a pharmaceutically acceptable form of iron in the disclosed nutritional compositions.

In the disclosed nutritional composition, it is preferable to include iron in the total amount of about 0.1 mg/kg to 6 mg/kg, 2.5 mg/kg to 5.5 mg/kg, 3 mg/kg to 5 mg/kg, 3.5 mg/kg to 4.5 mg/kg, or any range having endpoints falling within any of the preceding ranges of a subject's body mass. For example, if the subject has a body mass of 100 kg (i.e., 220 lbs), it is preferable to orally administer 10 mg to 600 mg of iron to this subject when using the 2 mg/kg to 6 mg/kg range. Total amounts of iron in the dietary supplement falling below 1 mg/kg are potentially inadequate to prevent or reduce problems associated with iron deficiency. Furthermore, total amounts of iron exceeding 6 mg/kg may be associated with unwanted side effects associated such as iron poisoning if administered for an extended period of time. Therefore, in certain aspects, the total amount of iron thereof present in the dietary supplement ranges from 10 mg to 600 mg, 10 mg to 500 mg, 10 mg to 400 mg, 10 mg to 300 mg, 10 mg to 200 mg, 10 mg to 100 mg, 50 mg to 500 mg, 50 mg to 400 mg, 50 mg to 300 mg, 50 mg to 200 mg, 50 mg to 100 mg, 100 mg to 500 mg, 100 mg to 450 mg, 100 mg to 400 mg, 100 mg to 350 mg, 100 mg to 300 mg, 100 mg to 250 mg, 100 mg to 200 mg, 100 mg to 150 mg, 200 mg to 400 mg, 200 mg to 350 mg, 200 mg to 300 mg, 200 mg to 250 mg, 300 mg to 500 mg, 300 mg to 450 mg, 300 mg to 400 mg, 300 mg to 350 mg, or any range having endpoints falling within any of the preceding ranges.

Iron may be provided through many different pharmaceutically acceptable salts or chelates and one skilled in the art would know of these salts and chelates. Some pharmaceutically acceptable forms of iron supplementation may be through carbonyl, ferrous gluconate, ferrous fumerate, iron amino acid complexes, ferronyl carbonate, iron chelates, among others not listed.

In certain aspects, the total amount of Iron present in the dietary supplement is about 27.5 mg. In certain aspects, the total amount of iron present in the dietary supplement ranges from 0.5 mg to 100 mg based on the total weight of the dietary supplement.

In certain aspects, iron is not included in the microparticles of the dietary supplement. In other aspects, a portion of iron is included in any of the coated layers of the microparticles and another portion of iron is included in the encapsulating body (e.g., tablets and capsules) that is not the microparticle. For example, in certain aspects, at least 90%, 85%, 80%, 75%, 70%, 65%, 60%, 55%, or 50% of the overall amount of iron is not in the microparticles, and in this aspect, the remainder of the iron can be included the microparticle.

Other Ingredients

In certain embodiments and as discussed further below, the disclosed dietary supplement can optionally include pharmaceutically acceptable Vitamin $B_6$, Vitamin $B_{12}$, N-Acetyl-L-Cysteine (NAC), Coenzyme Q10 (CoQ 10) or any combination thereof.

In certain embodiments, the disclosed nutritional composition can optionally include pharmaceutically acceptable Vitamin $B_6$. Vitamin $B_6$, and more specifically pyridoxal-5-phosphate, is involved in numerous biological reactions occurring in a subject including amino acid metabolism, hemoglobin synthesis, neurotransmitter synthesis, lipid metabolism, gluconeogenesis (e.g., glycogenolysis), and transsulphuration (e.g. homocysteine oxidation). Transsulphuration is the process by which homocysteine is oxidized to a sulphate anion; abnormality in this process (e.g. from low Vitamin $B_6$ levels) can lead to hyperhomocysteinaemia, which has been associated with several disease states including cardiovascular disorders, cognitive dysfunction, neurotoxicity, neuropsychiatric illness, and bone problems. Vitamin $B_6$ may also be supplemented as pyridoxine HCl. Other forms of Vitamin $B_6$ are known and one skilled in the art would be aware of the various forms. Thus, to further complement the effects of DHA, folic acid and derivatives thereof, and iron mentioned above, Vitamin $B_6$ can be added to the dietary supplement. In certain aspects, the total amount of Vitamin $B_6$ present in the dietary supplement ranges from 0.1 mg to 100 mg, 0.1 mg to 75 mg, 0.1 mg to 50 mg, 0.1 mg to 25 mg, 0.1 mg to 10 mg, 0.1 mg to 7.5 mg, 0.1 mg to 5 mg, 0.1 mg to 3 mg, 0.1 mg to 2.5 mg, 0.1 mg to 2 mg, 0.1 mg to 1 mg, 0.1 mg to 0.5 mg, 0.2 mg to 10 mg, 0.2 mg to 7.5 mg, 0.2 mg to 5 mg, 0.2 mg to 2.5 mg, 0.2 mg to 2.0 mg, 0.2 mg to 1.5 mg, 0.2 mg to 1 mg, 0.3 mg to 10 mg, 0.3 mg to 7.5 mg, 0.3 mg to 5 mg, 0.3 mg to 2.5 mg, 0.3 mg to 2.0 mg, 0.3 mg to 1.5 mg, 0.3 mg to 1 mg, 0.5 mg to 5 mg, 0.5 mg to 4 mg, 0.5 mg to 3 mg, 0.5 mg to 2.5 mg, 0.5 mg to 2.0 mg, 0.5 mg to 1.5 mg, 0.5 mg to 1 mg, 0.75 mg to 3 mg, 0.75 mg to 2.5 mg, 0.75 mg to 2.0 mg, 0.75 mg to 1.5 mg, 0.75 mg to 1 mg, 1 mg to 2 mg, 1 mg to 1.5 mg or any range having endpoints falling within any of the preceding ranges.

In certain aspects, the total amount of Vitamin $B_6$ present in the dietary supplement ranges from 0.5 mg to 55 mg based on the total weight of the dietary supplement. In one aspect, the total amount of Vitamin $B_6$ is 26 mg. In another aspect, the total amount of Vitamin $B_6$ is 35 mg. In one aspect, the total amount of Vitamin $B_6$ is 25 mg.

In certain aspects, Vitamin $B_6$ is not included in the microparticles of the nutritional composition. In other aspects, a portion of Vitamin $B_6$ is included in any of the coated layers of the microparticles and another portion of Vitamin $B_6$ is included in the encapsulating body (e.g., tablets and capsules) that is not the microparticle. For example, in certain aspects, at least 90%, 85%, 80%, 75%, 70%, 65%, 60%, 55%, or 50% of the overall amount of Vitamin B6 is not in the microparticles, and in this aspect, the remainder of Vitamin B6 can be included in the microparticle.

In certain embodiments, the disclosed dietary supplement can optionally include pharmaceutically acceptable Vitamin $B_{12}$. Vitamin $B_{12}$ plays a role in DNA synthesis, regulation of DNA synthesis, and fatty acid synthesis. Vitamin $B_12$ has been implicated in playing a key role in maintaining normal brain function and regulating the nervous system. In humans, Vitamin $B_{12}$ deficiency can cause severe and irreversible damage to the brain and nervous system, which may manifest with symptoms of mania and psychosis.

In persons with diabetes experiencing diabetic peripheral neuropathy, Vitamin $B_{12}$ supplementation has been shown to reduce pain and paresthesia.

Thus, to potentially prevent Vitamin $B_{12}$ deficiency and to further complement the effects of DHA, folic acid and derivatives thereof, and iron discussed above, Vitamin $B_{12}$ can be added to the dietary supplement. Vitamin $B_{12}$ may also be supplemented as cyanocobalamin, or preferably methylcobalamin. Other forms of Vitamin $B_{12}$ are known and one skilled in the art would be aware of the various forms.

In certain aspects, the total amount of Vitamin $B_{12}$ present in the dietary supplement ranges from 0.1 µg to 5 µg, 0.1 µg to 4 µg, 0.1 µg to 3 µg, 0.1 µg to 2 µg, 0.1 µg to 1 µg, 0.3 µg to 4.5 µg, 0.3 µg to 3.5 µg, 0.3 µg to 2.5 µg, 0.3 µg to 2 µg, 0.3 µg to 1 µg, 0.4 µg to 3.5 µg, 0.4 µg to 3 µg, 0.4 µg to 2.5 µg, 0.4 µg to 2 µg, 0.4 µg to 1 µg, 0.5 µg to 3 µg, 0.5 µg to 2.5 µg, 0.5 µg to 2 µg, 0.5 µg to 2 µg, 0.5 µg to 0.9 µg, or any range having endpoints falling within any of the preceding ranges. In certain aspects, the total amount of Vitamin $B_{12}$ present in the dietary supplement ranges from 10 µg to 5 mg based on the total weight of the dietary supplement. In one aspect, the total amount of Vitamin $B_{12}$ is 12 mcg. In another aspect, the total amount of Vitamin $B_{12}$ is 2 mg.

In certain aspects, Vitamin $B_{12}$ is not included in the microparticles of the nutritional composition. In other aspects, a portion of Vitamin $B_{12}$ is included in any of the coated layers of the microparticles and another portion of Vitamin $B_{12}$ is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin $B_{12}$ is not in the microparticles, and in this aspect, the remainder of Vitamin $B_{12}$ can be included in the microparticle.

In certain embodiments, the disclosed dietary supplement can optionally include pharmaceutically acceptable N-Acetyl-L-Cysteine in the range of from 100 mg to 1000 mg, 100 mg to 900 mg, 100 mg to 800 mg, 100 mg to 700 mg, 100 mg to 600 mg, 100 mg to 500 mg, 100 mg to 400 mg, 100 mg to 300 mg, 100 mg to 200 mg, 200 mg to 800 mg, 200 mg to 650 mg, 200 mg to 500 mg, 200 mg to 450 mg, 200 mg to 300 mg, 300 mg to 750 mg, 300 mg to 600 mg, 300 mg to 500 mg, 300 mg to 450 mg, 300 mg to 400 mg, 400 mg to 650 mg, 400 mg to 600 mg, 400 mg to 550 mg, 400 mg to 500 mg, 400 mg to 450 mg, or any range having endpoints falling within any of the preceding ranges.

In certain aspects, the total amount of N-Acetyl-L-Cysteine present in the dietary supplement ranges from 1 mg-1 g based on the total weight of the dietary supplement.

In certain aspects, N-Acetyl-L-Cysteine is not included in the microparticles of the nutritional composition. In other aspects, a portion of N-Acetyl-L-Cysteine is included in any of the coated layers of the microparticles and another portion of N-Acetyl-L-Cysteine is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of N-Acetyl-L-Cysteine is not in the microparticles, and in this aspect, the remainder of N-Acetyl-L-Cysteine can be included in the microparticle.

In certain embodiments, the disclosed dietary supplement can optionally include pharmaceutically acceptable Coenzyme Q10 (CoQ 10). CoQ 10 is a vitamin-like substance that is present primarily in mammalian mitochondria. In humans, CoQ10 has been implicated in oxidative phosphorylation and electron chain transport in the mitochondria, which ultimately results in the production of ATP. Furthermore, CoQ10 has an antioxidant function that reduces or prevents lipid peroxidation. Therefore, in certain aspects, CoQ10 may act synergistically with the DHA described herein as well as Vitamin $B_6$ and/or Vitamin $B_{12}$ to promote cognitive function by promoting lipid synthesis and lipid maintenance occurring, for example, in the brain while concurrently reducing lipid damage occurring from lipid peroxidation.

In certain aspects, the total amount of CoQ10 present in the dietary supplement ranges from 0.5 mg to 7 mg, 0.5 mg to 6 mg, 0.5 mg to 5 mg, 0.5 mg to 4 mg, 0.5 mg to 3 mg, 0.5 mg to 2 mg, 0.5 mg to 1 mg, 1 mg to 6.5 mg, 1 mg to 6 mg, 1 mg to 5.5 mg, 1 mg to 5 mg, 1 mg to 4.5 mg, 1 mg to 4 mg, 1 mg to 3.5 mg, 1 mg to 3 mg, 1 mg to 2.5 mg, 1 mg to 2 mg, 2 mg to 6 mg, 2 mg to 5.5 mg, 2 mg to 5 mg, 2 mg to 4.5 mg, 2 mg to 4 mg, 2 mg to 3.5 mg, 2 mg to 3 mg, 2 mg to 2.5 mg, 3 mg to 6 mg, 3 mg to 5.5 mg, 3 mg to 5 mg, 3 mg to 4.5 mg, 3 mg to 4 mg, 3 mg to 3.5 mg, 4 mg to 5.5 mg, 4 mg to 5 mg, 4 mg to 4.5 mg, or any range having endpoints falling within any of the preceding ranges. In certain aspects, the total amount of CoQ10 present in the dietary supplement ranges from 50 mg to 200 mg based on the total weight of the dietary supplement.

In certain aspects, CoQ10 is not included in the microparticles of the nutritional composition. In other aspects, a portion of CoQ10 is included in any of the coated layers of the microparticles and another portion of CoQ10 is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of CoQ10 is not in the microparticles, and in this aspect, the remainder of CoQ10 can be included in a portion of the encapsulating body that is not the microparticle.

In certain embodiments, the disclosed dietary supplement can optionally include pharmaceutically acceptable Vitamin C in the range of from 10 mg to 1000 mg.

In certain aspects, the total amount of Vitamin C present in the dietary supplement is about 70 mg.

In certain aspects, Vitamin C is not included in the microparticles of the nutritional composition. In other aspects, a portion of Vitamin C is included in any of the coated layers of the microparticles and another portion of Vitamin C is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin C is not in the microparticles, and in this aspect, the remainder of Vitamin C can be included in the microparticle.

In certain embodiments, the disclosed dietary supplement can optionally include pharmaceutically acceptable Vitamin D in the range of from 50 IU to 2000 IU.

In certain aspects, the total amount of Vitamin D present in the dietary supplement is about 1000 IU.

In certain aspects, Vitamin D is not included in the microparticles of the nutritional composition. In other aspects, a portion of Vitamin D is included in any of the coated layers of the microparticles and another portion of Vitamin D is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin D is not in the microparticles, and in this aspect, the remainder of Vitamin D can be included in the microparticle.

In certain embodiments, the disclosed nutritional composition can optionally include pharmaceutically acceptable Vitamin E in the range of from 10 IU to 1000 IU.

In certain aspects, the total amount of Vitamin E present in the nutritional composition is about 10 IU.

In certain aspects, Vitamin E is not included in the microparticles of the nutritional composition. In other aspects, a portion of Vitamin E is included in any of the coated layers of the microparticles and another portion of Vitamin E is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Vitamin E is not in the microparticles, and in this aspect, the remainder of Vitamin E can be included in the microparticle.

In certain embodiments, the disclosed dietary supplement can optionally include pharmaceutically acceptable Calcium in the range of from 5 mg to 200 mg. Calcium may be provided through many different pharmaceutically acceptable salts or chelates and one skilled in the art would know of these salts or chelates.

In certain aspects, the total amount of Calcium present in the dietary supplement is about 15 mg.

In certain aspects, Calcium is not included in the microparticles of the nutritional composition. In other aspects, a portion of Calcium is included in any of the coated layers of the microparticles and another portion of Calcium is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Calcium is not in the microparticles, and in this aspect, the remainder of Calcium can be included in the microparticle.

In certain embodiments, the disclosed dietary supplement can optionally include pharmaceutically acceptable Iodine in the range of from 50 mcg to 300 mcg. Iodine may be provided through many different pharmaceutically acceptable salts and one skilled in the art would know of these salts. In one aspect, iodine is provided as potassium iodide.

In certain aspects, the total amount of Iodine present in the dietary supplement is about 150 mcg.

In certain aspects, Iodine is not included in the microparticles of the nutritional composition. In other aspects, a portion of Iodine is included in any of the coated layers of the microparticles and another portion of Iodine is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Iodine is not in the microparticles, and in this aspect, the remainder of Iodine can be included in the microparticle.

In certain embodiments, the disclosed dietary supplement can optionally include pharmaceutically acceptable Magnesium in the range of from 5 mg to 100 mg. Magnesium may be provided through many different pharmaceutically acceptable salts and chelates and one skilled in the art would know of these salts and chelates. In one aspect, magnesium is provided as magnesium oxide.

In certain aspects, the total amount of Magnesium present in the dietary supplement is about 20 mg.

In certain aspects, Magnesium is not included in the microparticles of the nutritional composition. In other aspects, a portion of Magnesium is included in any of the coated layers of the microparticles and another portion of Magnesium is included in a portion of the encapsulating body (e.g., tablets and capsules) that is not the microparticle. For example, in certain aspects, at least 90%, 85%, 80%, 75%, 70%, 65%, 60%, 55%, or 50% of the overall amount of Magnesium is not in the microparticles, and in this aspect, the remainder of Magnesium can be included in the microparticle.

In addition, any standard pharmaceutically acceptable excipient can be used in the nutritional composition. For example, these excipients can include diluents (e.g., mannitol, sorbitol, lactose, sucrose, and compressible sugars such as DiPac™ (dextrinized sucrose), available from Austin Products Inc., Holmdel, N.J.), splitting or swelling agents (e.g., polyvinyl polypyrrolidone, croscarmellose sodium (e.g., Ac-Di-Sol™ available from FMC BioPolymer, Philadelphia, Pa.), starches and derivatives, cellulose and derivatives, microcrystalline celluloses, such as Avicel™ PH 101 or Avicel™ CE-15 (a microcrystalline modified with guar gum), both available from FMC BioPolymer, Philadelphia, Pa.), lubricating agents (e.g., magnesium stearate), and flow agents (e.g., colloidal silicon dioxide, such as Cab-O-Sil M5 available from Cabot Corporation, Kokomo, Ind.).

The phospholipid extract as a raw material can be provided in a dietary supplement as a natural product extracted from egg without any additional compounds. In some aspects the phospholipid extract may be blended with an antioxidant or other stabilizer for preservation; however, in another aspect, the phospholipid extract is not mixed with additional excipients but is simply added to a dietary supplement. If the phospholipid extract is not mixed with antioxidants, stabilizers, or excipients, refrigerating the phospholipid extract will improve stability and shelf life.

Other DHA raw ingredients used for nutritional supplementation (sourced from fish, algae, and krill) are mixed with many excipients and powders and the actual DHA content is only about 10% of the raw ingredient by weight. Thus, 100 mg of some DHA powders only actually provide 10 mg of DHA. The phospholipid extract provides more potent nutritional supplementation since a 100 mg amount of phospholipid extract would provide 20 mg of DHA, and the rest of the supplement would contain other phospholipids, which do provide nutritional benefit that the other powders would not.

Also, sweeteners can be included in the dietary supplement described herein. For example, sweeteners can be used to impart a pleasant flavor to the composition. Suitable sweeteners for use in the present disclosure include natural sweeteners such as sucrose, dextrose, fructose, invert sugar, mannitol, sorbitol, and the like, as well as synthetic sweeteners such as saccharin, aspartame, acesulfame potassium, cyclamates, and other commercial artificial sweeteners well-known to those of skill in the art. A preferred sweetener is acesulfame K (Sunett™ available from Nutrinova, Frankfort, Germany). The sweetener is added in an amount to achieve a desired sweetness. Typically, the sweetener is present in an amount from about 1.0 wt % to about 5.0 wt % of the overall weight of the nutritional composition. Since the dietary supplement may capitalize on the DHA being sourced from eggs, egg-friendly flavors are also preferred, which include vanilla and dulce de leche or caramel. Other flavors as chocolate or strawberry are also workable. Those skilled in the part will appreciate that the amount of sweetener may vary depending on the strength of the particular sweetener used and the levels approved by the regulatory authorities for use in pharmaceutical products.

Time Release Coatings

In certain aspects, the outermost surface of the encapsulating body and the outermost surface of the microparticle can independently include a time release coating. For example, in certain aspects the outermost surface of the encapsulating body can include a time release coating while such a coating is omitted from the microparticle. In other aspects, the outermost surface of the microparticle can include a time release coating while such a coating is omitted from the outermost surface of the encapsulating body.

Examples of these time release agents can include but are not limited to hydroxypropyl cellulose, hydroxypropyl methyl cellulose, hydroxypropyl methyl cellulose phthalate, pullulan, gelatin, collagen, casein, agar, gum arabic, dextrin, ethyl cellulose, methyl cellulose, chitin, chitosan, mannan, carboxymethylethyl cellulose, sodium carboxymethyl cellulose, polyethylene glycol, sodium alginate, poly(vinyl alcohol), cellulose acetate, poly(vinylpyrrolidone), silicone, poly (vinyl acetal) diethylamino acetate, albumin, adenine, cystine, D-tyrosine, or any combination thereof.

In certain aspects, these time release coatings may range from 1-15% of the overall weight of the dietary supplement.

EXAMPLES

Example 1

Microparticles Coated with Phospholipid Extract

Microparticle cores can be prepared by extrusion spheronizer technology, and the microparticle cores can be subsequently made of phospholipid extract, cellulose, starch, lactose, mannitol. PL-DHA may comprise 25% to 50% of the microparticle core.

A pharmaceutically acceptable source of phospholipid extract may be mixed with a pharmaceutically acceptable neutral material such as tartaric acid, sugar sphere, calcium carbonate, mannitol, microcrystalline cellulose, silica, or starch which is then subjected to an extruding step to obtain microparticle cores in which 95% of the microparticle cores have an average particle diameter ranging from 90 µm to 500 um. These materials are mixed for 15-25 minutes and then extruded out an extruder.

Next, the microparticle cores are placed into a spheroidizer at 500 rpm for 5 to 10 second to ensure that sufficient microparticle core roundness is obtained.

After ensuring proper microparticle core roundness has been obtained, the microparticle cores are organized into a bed of microparticle cores that are subjected to a coating step. Next, the microparticle cores may also be (i) directly coated with an enteric coating to provide a dissolution rate profile and/or (ii) directly coated with a protective coating: solution, suspension, or dispersion or. The enteric coating may be L30D on different polymers. The enteric coating may comprise 1-5% of the weight of the total microparticle composition. The protective coating maybe hpmc. The protective coating may comprise 1-10% of the weight of the total microparticle composition.

Example 2

Exemplary Nutritional Composition Formulations

Table 1 lists exemplary formulations of the dietary supplement of the present disclosure. The list is exemplary only and this disclosure is not limited to the examples below.

TABLE 1

| Ingredient | Exemplary Formulation 1 (wt %) | Exemplary Formulation 2 (wt %) | Exemplary Formulation 3 (wt %) | Exemplary Formulation 4 (wt %) |
|---|---|---|---|---|
| Total Egg Phospholipid ("Phospholipid extract")† | 200 mg | 50-250 mg | 90-95 mg | 50-250 mg |
| PC-DHA | 20 mg | 9 mg | 9 mg | 5-25 mg |
| PE-DHA | 5 mg | 4.5 mg | 4.5 mg | 5-25 mg |
| Folic Acid or other folate (total folate) | 1 mg | 3 mg | 6 mg | 15 mg |
| Iron | 27.5 mg | 0 mg | 0 mg | 0 mg |
| Vitamin $B_6$ (any form) | 26 mg | 25-35 mg | 0 mg | 0 mg |
| Vitamin E | 20 IU | 0 mg | 0 mg | 0 mg |
| Vitamin $B_{12}$ (any form) | 12 mcg | 2 mg | 2 mg | 0 mg |
| Calcium | 15 mg | 0 mg | 0 mg | 0 mg |
| NAC (any form) | 0 mg | 0 mg | 600 mg | 0 mg |

The formulations above do not include excipients, binders, stabilizers, etc.

Example 3

Single Ingredient DHA Supplement

The dietary supplement of the present disclosure may provide a phospholipid extract formulated as a single ingredient provided in a tablet, softgel, capsule, chewable, or gummy. The phospholipid extract may be provided as a single ingredient dietary supplement in the ranges from 50 mg to 1000 mg, 100 mg to 900 mg, 100 mg to 800 mg, 100 mg to 700 mg, 100 mg to 600 mg, 100 mg to 500 mg, 100 mg to 400 mg, 100 mg to 300 mg, 100 mg to 200 mg, 200 mg to 800 mg, 200 mg to 650 mg, 200 mg to 500 mg, 200 mg to 450 mg, 200 mg to 300 mg, 300 mg to 750 mg, 300 mg to 600 mg, 300 mg to 500 mg, 300 mg to 450 mg, 300 mg to 400 mg, 400 mg to 650 mg, 400 mg to 600 mg, 400 mg to 550 mg, 400 mg to 500 mg, 400 mg to 450 mg, or any range having endpoints falling within any of the preceding ranges.

The foregoing description provides embodiments of the disclosure by way of example only. It is envisioned that other embodiments may perform similar functions and/or achieve similar results. Any and all such equivalent embodiments and examples are within the scope of the present disclosure and are intended to be covered by the appended claims It should be emphasized that the embodiments described herein are merely possible examples of implementations, merely set forth for a clear understanding of the principles of the present disclosure. Many variations and modifications may be made to the described embodiment(s) without departing substantially from the spirit and principles of the present disclosure. Further, the scope of the present disclosure is intended to cover any and all combinations and sub-combinations of all elements, features, and aspects discussed above. All such modifications and variations are intended to be included herein within the scope of the present disclosure, and all possible claims to individual aspects or combinations of elements or steps are intended to be supported by the present disclosure.

One should note that conditional language, such as, among others, "can," "could," "might," or "may," unless specifically stated otherwise, or otherwise understood within the context as used, is generally intended to convey that certain embodiments include, while alternative embodiments do not include, certain features, elements and/or steps. Thus, such conditional language is not generally intended to imply that features, elements and/or steps are in any way required for one or more particular embodiments or that one or more particular embodiments necessarily include logic for deciding, with or without user input or prompting, whether these features, elements and/or steps are included or are to be performed in any particular embodiment. Unless stated otherwise, it should not be assumed that multiple features, embodiments, solutions, or elements address the same or related problems or needs.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

What is claimed is:

1. A manufactured composition comprising: a phospholipid extract at a concentration ranging from 50 mg to 500 mg, the phospholipid extract having phosphatidylcholine-docosahexaenoic acid and phosphatidylethanolamine-docosahexaenoic acid at a ratio ranging from 1:1 to 2:1, and
    a pharmaceutically acceptable form of reduced folate salt,
    a pharmaceutically acceptable form of vitamin $B_6$, and
    a pharmaceutically acceptable form of vitamin $B_{12}$.

2. The manufactured composition of claim 1, wherein the reduced folate is an L-Methylfolate.

3. The manufactured composition of claim 1, wherein the amount of vitamin $B_6$ is between about 25 mg and about 35 mg.

4. The manufactured composition of claim 1, wherein the amount of vitamin $B_{12}$ is between about 1 mg and about 2 mg.

5. The manufactured composition of claim 1, wherein the reduced folate is L-Methylfolate calcium.

6. The manufactured composition of claim 1, wherein the form of vitamin $B_6$ is pyridoxal-5-phosphate.

7. The manufactured composition of claim 1, wherein the form of vitamin $B_{12}$ is methylcobalamin.

8. The manufactured composition of claim 1, wherein the phospholipid extract contains less than 5%, by weight, triglycerides.

9. The manufactured composition of claim 1, wherein the phospholipid extract contains less than 0.5%, by weight, free fatty acids.

10. The manufactured composition of claim 1, wherein the phospholipid extract is substantially free of phosphatidylserine.

11. The manufactured composition of claim 1, wherein the phospholipid extract is substantially free of eicosapentaenoic acid.

12. The manufactured composition of claim 1, wherein the phospholipid extract is derived from non-genetically modified organism.

13. The manufactured composition of claim 1, wherein between about 5% and about 15% of the phospholipid extract is phosphatidylcholine-docosahexaenoic acid.

14. The manufactured composition of claim 1, wherein between about 5% and about 15% of the phospholipid extract is phosphatidylethanolamine-docosahexaenoic acid.

15. The manufactured composition of claim 1, wherein at least about 20% of the phospholipid extract, by weight, is phospholipid-docosahexaenoic acid.

16. The manufactured composition of claim 1, wherein the manufactured composition is a tablet, softgel, capsule, or chewable.

17. The manufactured composition of claim 1, wherein the phospholipid extract comprises less than 1.5% eicosapentaenoic acid by weight.

18. A manufactured composition consisting of: a phospholipid extract at a concentration ranging from about 50 mg to about 500 mg, the phospholipid extract having phosphatidylcholine-docosahexaenoic acid and phosphatidylethanolamine-docosahexaenoic acid at a ratio ranging from 1:1 to 2:1,
    about 3 mg of a pharmaceutically acceptable form of reduced folate,
    between about 25 mg and about 35 mg of a pharmaceutically acceptable form of vitamin $B_6$, and
    about 2 mg of a pharmaceutically acceptable form of vitamin $B_{12}$.

19. The manufactured composition of claim 1, additionally comprising:
    a pharmaceutically acceptable form of Vitamin D in the amount of between about 500 IU and about 1000 IU,
    wherein the amount of phospholipid extract is about 150 mg and the amount of phosphatidylcholine-docosahexaenoic acid is about 15 mg and the amount of phosphatidylethanolamine-docosahexaenoic acid is about 15 mg,
    wherein the reduced folate is a mixture of an L-Methylfolate and a folinic acid salt and the total amount of reduced folate is about 3 mg,
    wherein the vitamin $B_6$ is pyridoxal-5-phosphate in the amount of about 25 mg, and
    wherein the amount of vitamin $B_{12}$ is about 1 mg.

* * * * *